United States Patent
Xu et al.

(10) Patent No.: US 11,485,722 B2
(45) Date of Patent: *Nov. 1, 2022

(54) CYCLOPENTA[C]CHROMIUM COMPOUND AND PREPARATION METHOD THEREFOR

(71) Applicant: SOOCHOW UNIVERSITY, Suzhou (CN)

(72) Inventors: Fan Xu, Suzhou (CN); Xiaoyou Ding, Suzhou (CN); Dandan Li, Suzhou (CN); Yanan Zhu, Suzhou (CN); Zhigang Yao, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 88 days.

This patent is subject to a terminal disclaimer.

(21) Appl. No.: 17/163,479

(22) Filed: Jan. 31, 2021

(65) Prior Publication Data

US 2021/0147376 A1 May 20, 2021

Related U.S. Application Data

(63) Continuation of application No. PCT/CN2018/097756, filed on Jul. 30, 2018.

(51) Int. Cl.
*C07D 311/94* (2006.01)
*B01J 27/26* (2006.01)

(52) U.S. Cl.
CPC ............ *C07D 311/94* (2013.01); *B01J 27/26* (2013.01)

(58) Field of Classification Search
CPC .................................................... C07D 311/94
USPC .......................................................... 549/385
See application file for complete search history.

(56) References Cited

FOREIGN PATENT DOCUMENTS

CN         108774207 A      11/2018

OTHER PUBLICATIONS

Wang et al., "Iron-Mediated [3+2] or [3+3] Annulation of 2-(2-(Ethynyl)phenoxy)-1-arylethanones: Selective Synthesis of Indeno[1,2-c]chromenes and 5H-Naphtho[1,2-c]chromenes" Organic Letters, 2011 vol. 13, No. 1, 14-17 Jan. 12, 2010).

Luo et al., "Efficient generation of indeno[1,2-c]chromenes via the Pd-catalyzed reaction of 2-alkynylhalobenzenes with 2-alkynylphenols" Chem. Commun., 2011, 47, 5298-5300 (Mar. 31, 2011).

*Primary Examiner* — Taofiq A Solola

(74) *Attorney, Agent, or Firm* — SZDC Law P.C.

(57) ABSTRACT

The present invention discloses a cyclopenta[c]chromene compound and a preparation method thereof. A chalcone compound as a reactant, A cationic rare earth metal compound $Ln(CH_3CN)_9]^{3+}[(AlCl_4)_3]^{3-} \cdot CH_3CN$ as a catalyst, and 2-naphthalenethiol as an accelerator, react in an organic solvent to prepare the cyclopenta[c]-chromene compound. Ln represents a positive trivalent rare earth metal ion, which is selected from the group consisting of La, Nd, Sm, Gd, and Yb. The starting materials are easy obtained, the reaction process is simple, and the yield of the target product is high, up to 85%.

7 Claims, No Drawings

CYCLOPENTA[C]CHROMIUM COMPOUND AND PREPARATION METHOD THEREFOR

This application is a Continuation Application of PCT/CN2018/097756, filed on Jul. 30, 2018, which is incorporated by reference for all purposes as if fully set forth herein.

DESCRIPTION

Technical Field

The present invention relates to the technical field of preparation of organic oxa-fused ring compounds, and particularly a cyclopenta[c]chromene compound and a preparation method therefor.

Background Technique

Cyclopenta[c]chromene is an important class of oxa-fused ring compounds. Most of the compounds containing cyclopenta[c]chromene structure have good biological activity. At the same time, cyclopenta[c]chromene is also an important precursor compound for synthesizing many biologically active natural products (such as 11-oxasteroid compounds). Therefore, developing an effective method for synthesizing the cyclopenta[c]chromene skeleton has important theoretical and practical significance.

In the conventional art, reported synthetic routes of the cyclopenta[c]chromene skeleton are relatively limited. The main routes are: 1. hetero [6+3] of mono-, 6-dimethylaminofulvene and benzoquinone cycloaddition reaction (see Hong, B.; Chen, Z.; Chen, W. Org. Lett. 2000, 17, 2647.); 2. Palladium-catalyzed reaction of b-haloalkyne and 2-alkynylphenol (see Luo, Y; Hong, L.; Wu, J. Chem. Commun. 2011, 47, 5298.); 3. 2-(2-(ethynyl) phenoxy)-1-arylethyl ketone [3+2] cycloaddition reaction (see Wang, Z.; Lei, Y; Zhou, M.; Chen, G.; Song, R.; Xie, Y; Li, J. Org. Lett. 2011, 13, 14.).

Technical Problem

The common feature of these synthetic routes is that the substrates are relatively complicated, mostly involving aryl mono- and di-yne compounds, and often requiring noble metal catalysts or strong bases, and the yields are mostly low, so they have certain limitations. More importantly, in these methods, cyclopenta[c]chromene compounds can be obtained in a few instances, and indeno[c]chromene compounds are usually the final products. The research on the synthesis of the cyclopenta[c]chromene compounds is very limited. In view of the good biological activity of the cyclopenta[c]chromene-containing compounds, a simple, highly active, universal, and catalytic method for the synthesis of cyclopentadiene[c]chromene compound is necessary.

Technical Solutions

In order to achieve the above-mentioned objects of the invention, the technical solutions adopted by the present invention are:

A method for preparing cyclopenta[c]chromene compound includes the following steps: under anhydrous and anaerobic conditions, a chalcone compound as a reactant, a cationic rare earth metal compound as a catalyst, and 2-naphthalenethiol as an accelerator, react in an organic solvent to prepare the cyclopenta[c]chromene compound. The cationic rare earth metal compound has the following structure:

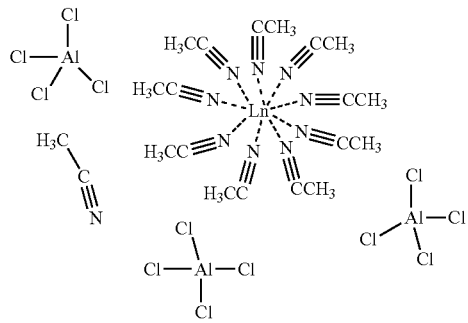

Ln represents a trivalent rare earth metal ion;
The chalcone compound has the following chemical structure:

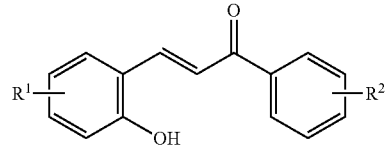

$R^1$ is selected from the group consisting of hydrogen, 3-chloro, 4-chloro, 4-methoxy, 5-chloro, 5-bromo, 5-methyl, 5-methoxy, and 6-chloro; $R^2$ is selected the group consisting of hydrogen, 3'-chloro, 3'-bromo, 3'-methoxy, 4'-chloro, 4'-bromo, 4'-phenyl, and 4'-methoxy.

In the above technical solution, preferably, the anhydrous and anaerobic conditions are an inert atmosphere condition.

In the above technical solution, the organic solvent is selected from the group consisting of chlorobenzene, acetonitrile, dichloroethane, and toluene, preferably, chlorobenzene. Under the same conditions, compared to the other four metals, the reaction catalyzed by it has a higher yield for the formation of cyclopenta[c]chromene In the above technical solution, the general formula of the cationic rare earth metal compound is: $[Ln(CH_3CN)_9]^{3+}[(AlCl_4)_3]^{3-} \cdot CH_3CN$; wherein Ln represents the positive trivalent rare earth metal ion, selected from one of lanthanum, neodymium, samarium, gadolinium, or ytterbium, preferably ytterbium. Under the same conditions, compared to the other four metals, ytterbium leads a higher yield for the formation of cyclopenta[c]chromene.

In the above technical solution, the amount of the catalyst used is 1 to 8%, preferably 3 to 7%, and more preferably 3%, of the moles of the chalcone compound. The reaction can be performed efficiently and the reaction cost is low.

In the above technical solution, the amount of 2-naphthalenethiol is 0.6 to 1.3 times, preferably 1.1 to 1.2 times, and most preferably 1.2 times, of the moles of the chalcone compound. If the amount of 2-naphthalenethiol is too small, the reaction cannot be performed efficiently. If the amount is too large, the starting materials will be wasted and the post-treatment of the reaction will be complicated.

In the above technical solution, the reaction temperature is 80 to 140° C., preferably, the reflux temperature of the organic solvent, and more preferably, the reflux temperature of chlorobenzene; and the reaction time is 24 to 72 hours, preferably, 36 hours.

To prepare cyclopenta[c]chromene compound by the preparation method for cyclopenta[c]chromene compound.

The invention also discloses the application of a cationic rare earth metal compound and 2-naphthalenethiol thiophenol in the preparation of a cyclopenta[c]chromene compound, or a chalcone compound in the preparation of a cyclopentadiene [c] chromene compound. In the application, a cationic rare earth metal compound is preferably used as a catalyst. In the presence of 2-naphthalenethiol thiophenol, a chalcone compound is used in the preparation of a cyclopenta[c]chromene compound.

The invention also discloses the application of 2-naphthalenethiol thiophenol as a promoter in the preparation of a cyclopentadien [c] chromene compound in the presence of a cationic rare earth metal compound.

In the present invention, the cyclopenta[c]chromene compound has the following chemical structure:

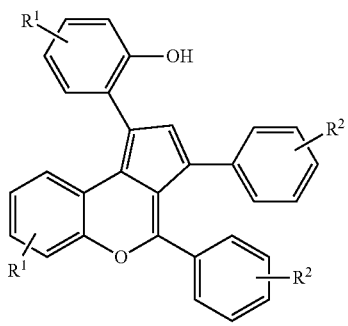

In the above technical solution, the reaction process includes mixing chalcones, cationic rare earth metal compounds $[Ln(CH_3CN)_9]^{3+}[(AlCl_4)_3]^{3-}.CH_3CN$ in a solvent, stirring for a few minutes, then adding 2-naphthalenethiol and a small amount of solvent, mixing and stirring at 80 to 140° C. for 24 to 72 hours, quenching the reaction, performing extraction, drying the extract with a drying agent, filtering, and removing the solvent under pressure, and finally running a silica gel flash column chromatography to obtain the cyclopenta[c]chromene.

In the above technical solution, operations, such as quenching the reaction, extracting, removing the solvent under reduced pressure, and finally obtaining cyclopenta[c] chromene by silica gel flash column chromatography, are known in the art. The extraction agent used therein, drying agent and eluents are also known. Those skilled in the art can select appropriate agents according to the properties of the final product. In a preferred technical solution, the reaction is quenched with water, the extractant is ethyl acetate, the drying agent is anhydrous sodium sulfate, and the eluent is ethyl acetate/petroleum ether system (volume ratio is 1:20 to 1:15).

The above technical solution can be expressed as follows:

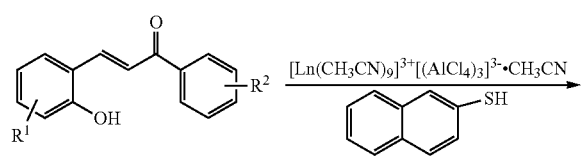

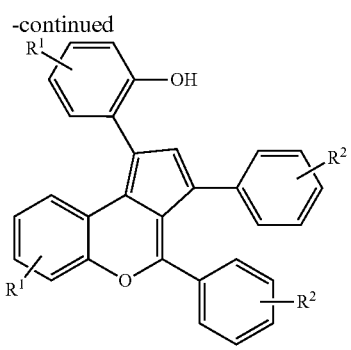

Beneficial Effect

Due to the application of the above technical solutions, the present invention has the following advantages over the prior art:

1. The present invention uses the cationic rare earth metal compound $[Ln(CH_3CN)_9]^{3+}[(AlCl_4)_3]^{3-}.CH_3CN$ as catalyst for the first time to catalyze the reaction of chalcone compounds to prepare cyclopentadien[c]chromene compounds, and the starting materials are easy obtained, the reaction process is simple, and the yield of the target product is high, up to 85%;

2. The method disclosed by the invention uses a small amount of catalyst and a simple post-treatment method, and the purification of the product is also convenient;

3. The catalyst disclosed in the present invention is applicable to a variety of substituted chalcone compounds, and cyclopentadieno[c]chromene compounds obtained have not been reported;

4. The catalytic synthesis method used in the invention is simple and easy to carry out;

5. The method disclosed in the present invention does not use a noble metal catalyst and does not use a strong base, the reaction cost is low, and the environment is protected.

EMBODIMENTS OF THE INVENTION

The following further describes the present invention with reference to the embodiments:

Example 1: Synthesis of Catalyst $[Yb(CH_3CN)_9]^{3+}$ $[(AlCl_4)_3]^{3-}.CH_3CN$ Under the protection of argon, 0.70 g (2.5 mmol) of $YbCl_3$ and 1.00 g (7.5 mmol) of anhydrous AlCl3 were added into a dehydrated and deoxidized reaction flask according in a molar ratio of 1:3. 25 mL of acetonitrile was added to dissolve reactants. Centrifugal treatment was carried out after stirring for 24 hours at room temperature, taking the supernatant, concentrating and leaving it in a refrigerator at 0° C. The obtained crystal is $[Yb(CH_3CN)_9]^{3+}$ $[(AlCl_4)_3]^{3-}.CH_3CN$, yield 46%.

Other $[Ln(CH_3CN)_9]^{3+}[(AlCl_4)_3]^{3-}.CH_3CN$ catalysts can be prepared by the same method, using different rare earth metal chloride.

Example 2: $[Yb(CH_3CN)_9]^{3+}[(AlCl_4)_3]^{3-}.CH_3CN$ Catalyzed Reaction of 2-Hydroxychalcone to Prepare Cyclopenta[c]Chromene Compound $[Yb(CH_3CN)_9]^{3+}[(AlCl_4)_3]^{3-}.CH_3CN$ (0.0163 g, 0.015 mmol, 3 mol %), 2-hydroxychalcone (0.1121 g, 0.5 mmol) and chlorobenzene (1 mL) were added into a dehydrated and deoxidized reaction flask, stirred for 2 minutes. 2-Naphthalenethiol (0.0961 g, 0.6 mmol) and chlorobenzene (1 mL) were then added, stirred and refluxed for 24 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 46%.

The theoretical molecular formula and NMR spectrum of the product obtained are shown below. It can be seen from the analysis that the actual synthesized product is consistent with the theoretical analysis.

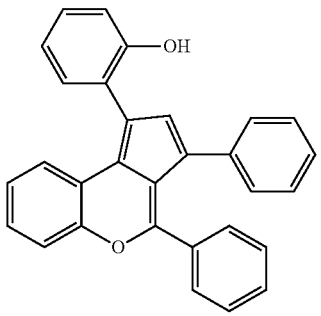 [SMILES: Oc1ccccc1-c1cc(-c2ccccc2)c2c(-c3ccccc3)oc3ccccc3c1-2]

$^1$H NMR (400 MHz, CDCl$_3$) δ 7.70 (d, J=8.0 Hz, 1H), 7.60 (d, J=8.4 Hz, 1H), 7.47-7.44 (m, 3H), 7.37-7.28 (m, 3H), 7.24-7.20 (m, 1H), 7.16-7.13 (m, 2H), 7.11-7.04 (m, 3H), 7.02-6.96 (m, 5H), 5.42 (s, 1H).

Example 3: [Yb(CH$_3$CN)$_9$]$^{3+}$[(AlCl$_4$)$_3$]$^{3-}$·CH$_3$CN Catalyzed Reaction of 2-Hydroxychalcone to Prepare Cyclopenta[c]Chromene Compound

[Yb(CH$_3$CN)$_9$]$^{3+}$[(AlCl$_4$)$_3$]$^{3-}$·CH$_3$CN (0.0381 g, 0.035 mmol, 7 mol %), 2-hydroxychalcone (0.1121 g, 0.5 mmol) and chlorobenzene (1 mL) were added into a dehydrated and deoxidized reaction flask, and stirred for 2 minutes. 2-Naphthalenethiol (0.0961 g, 0.6 mmol) and chlorobenzene (1 mL) were added, stirred and refluxed for 24 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 87%.

Example 4: [Yb(CH$_3$CN)$_9$]$^{3+}$[(AlCl$_4$)$_3$]$^{3-}$·CH$_3$CN Catalyzed Reaction of 2-Hydroxychalcone to Prepare Cyclopenta[c]Chromene Compound

[Yb(CH$_3$CN)$_9$]$^{3+}$[(AlCl$_4$)$_3$]$^{3-}$·CH$_3$CN (0.0163 g, 0.015 mmol, 3 mol %), 2-hydroxychalcone (0.1121 g, 0.5 mmol) and chlorobenzene (1 mL) were added into a dehydrated and deoxidized reaction flask, and stirred for 2 minutes. 2-Naphthalenethiol (0.0961 g, 0.6 mmol) and chlorobenzene (1 mL) were added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 85%. When the catalyst was changed to "3% YbCl$_{3+}$9% AlCl$_3$," "3% YbCl$_3$," or "3% FeCl$_3$," the yield was 59%, 30%, or 27% respectively. When the accelerator was changed to 1-mercaptodecane, the yield was 24%.

Example 5: [Yb(CH$_3$CN)$_9$]$^{3+}$[(AlCl$_4$)$_3$]$^{3-}$·CH$_3$CN Catalyzed Reaction of 2-Hydroxychalcone to Prepare Cyclopenta[c]Chromene Compound

[Yb(CH$_3$CN)$_9$]$^{3+}$[(AlCl$_4$)$_3$]$^{3-}$·CH$_3$CN (0.0163 g, 0.015 mmol, 3 mol %), 2-hydroxychalcone (0.1121 g, 0.5 mmol) and chlorobenzene (1 mL) were added into a dehydrated and deoxidized reaction flask, and stirred for 2 minutes. 2-Naphthalenethiol (0.0961 g, 0.6 mmol) and chlorobenzene (1 mL) were added, stirred and refluxed for 60 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 81%.

Example 6: [Yb(CH$_3$CN)$_9$]$^{3+}$[(AlCl$_4$)$_3$]$^{3-}$·CH$_3$CN Catalyzed Reaction of 2-Hydroxychalcone to Prepare Cyclopenta[c]Chromene Compound

[Yb(CH$_3$CN)$_9$]$^{3+}$[(AlCl$_4$)$_3$]$^{3-}$·CH$_3$CN (0.0163 g, 0.015 mmol, 3 mol %), 2-hydroxychalcone (0.1121 g, 0.5 mmol) and chlorobenzene (1 mL) were added into a dehydrated and deoxidized reaction flask, and stirred for 2 minutes. 2-Naphthalenethiol (0.0961 g, 0.6 mmol) and chlorobenzene (1 mL) were added, stirred and refluxed for 72 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 76%.

Example 7: [Yb(CH$_3$CN)$_9$]$^{3+}$[(AlCl$_4$)$_3$]$^{3-}$·CH$_3$CN Catalyzed Reaction of 2-Hydroxychalcone to Prepare Cyclopenta[c]Chromene Compound

[Yb(CH$_3$CN)$_9$]$^{3+}$[(AlCl$_4$)$_3$]$^{3-}$·CH$_3$CN (0.0163 g, 0.015 mmol, 3 mol %), 2-hydroxychalcone (0.1121 g, 0.5 mmol) and acetonitrile (1 mL) were added into a dehydrated and deoxidized reaction flask, and stirred for 2 minutes. 2-Naphthalenethiol (0.0961 g, 0.6 mmol) and acetonitrile (1 mL) were added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 47%.

Example 8: $[Yb(CH_3CN)_9]^{3+}[(AlCl_4)_3]^{3-} \cdot CH_3CN$ Catalyzed Reaction of 2-Hydroxychalcone to Prepare Cyclopenta[c]Chromene Compound $[Yb(CH_3CN)_9]^{3+}[(AlCl_4)_3]^{3-} \cdot CH_3CN$ (0.0163 g, 0.015 mmol, 3 mol %), 2-hydroxychalcone (0.1121 g, 0.5 mmol) and dichloroethane (1 mL) were added into a dehydrated and deoxidized reaction flask, and stirred for 2 minutes. 2-Naphthalenethiol (0.0961 g, 0.6 mmol) and dichloroethane (1 mL) were added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 46%.

Example 9: $[Yb(CH_3CN)_9]^{3+}[(AlCl_4)_3]^{3-} \cdot CH_3CN$ Catalyzed Reaction of 2-Hydroxychalcone to Prepare Cyclopenta[c]Chromene Compound $[Yb(CH_3CN)_9]^{3+}[(AlCl_4)_3]^{3-} \cdot CH_3CN$ (0.0163 g, 0.015 mmol, 3 mol %), 2-hydroxychalcone (0.1121 g, 0.5 mmol) and toluene (1 mL) were added into a dehydrated and deoxidized reaction flask, and stirred for 2 minutes. 2-Naphthalenethiol (0.0961 g, 0.6 mmol) and toluene (1 mL) were added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 43%.

Example 10: $[Yb(CH_3CN)_9]^{3+}[(AlCl_4)_3]^{3-} \cdot CH_3CN$ Catalyzed Reaction of 2-Hydroxychalcone to Prepare Cyclopenta[c]Chromene Compound $[Yb(CH_3CN)_9]^{3+}[(AlCl_4)_3]^{3-} \cdot CH_3CN$ (0.0163 g, 0.015 mmol, 3 mol %), 2-hydroxychalcone (0.1121 g, 0.5 mmol) and chlorobenzene (1 mL) were added into a dehydrated and deoxidized reaction flask, and stirred for 2 minutes. 2-Naphthalenethiol (0.0961 g, 0.6 mmol) and chlorobenzene (1 mL) were added, stirred at 100° C. for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 64%.

Example 11: $[Yb(CH_3CN)_9]^{3+}[(AlCl_4)_3]^{3-} \cdot CH_3CN$ Catalyzed Reaction of 2-Hydroxychalcone to Prepare Cyclopenta[c]Chromene Compound $[Yb(CH_3CN)_9]^{3+}[(AlCl_4)_3]^{3-} \cdot CH_3CN$ (0.0163 g, 0.015 mmol, 3 mol %), 2-hydroxychalcone (0.1121 g, 0.5 mmol) and chlorobenzene (1 mL) were added into a dehydrated and deoxidized reaction flask, and stirred for 2 minutes. 2-Naphthalenethiol (0.0961 g, 0.6 mmol) and chlorobenzene (1 mL) were added, stirred at 120° C. for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 80%.

Example 12: $[Yb(CH_3CN)_9]^{3+}[(AlCl_4)_3]^{3-} \cdot CH_3CN$ Catalyzed Reaction of 2-Hydroxychalcone to Prepare Cyclopenta[c]Chromene Compound $[Yb(CH_3CN)_9]^{3+}[(AlCl_4)_3]^{3-} \cdot CH_3CN$ (0.0163 g, 0.015 mmol, 3 mol %), 2-hydroxychalcone (0.1121 g, 0.5 mmol) and chlorobenzene (1 mL) were added into a dehydrated and deoxidized reaction flask, and stirred for 2 minutes. 2-Naphthalenethiol (0.0481 g, 0.3 mmol) and chlorobenzene (1 mL) were added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 61%.

Example 13: $[Yb(CH_3CN)_9]^{3+}[(AlCl_4)_3]^{3-} \cdot CH_3CN$ Catalyzes the Reaction of 2-Hydroxychalcone to Prepare Cyclopenta[c]Chromene Compound $[Yb(CH_3CN)_9]^{3+}[(AlCl_4)_3]^{3-} \cdot CH_3CN$ (0.0163 g, 0.015 mmol, 3 mol %), 2-hydroxychalcone (0.1121 g, 0.5 mmol) and chlorobenzene (1 mL) were added into a dehydrated and deoxidized reaction flask, and stirred for 2 minutes. 2-Naphthalenethiol (0.0801 g, 0.5 mmol) and chlorobenzene (1 mL) were added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 63%.

Example 14: $[Yb(CH_3CN)_9]^{3+}[(AlCl_4)_3]^{3-} \cdot CH_3CN$ Catalyzed Reaction of 2-Hydroxychalcone to Prepare Cyclopenta[c]Chromene Compound $[Yb(CH_3CN)_9]^{3+}[(AlCl_4)_3]^{3-} \cdot CH_3CN$ (0.0163 g, 0.015 mmol, 1 mol %), 2-hydroxychalcone (0.1121 g, 0.5 mmol) and chlorobenzene (1 mL) were added into a dehydrated and deoxidized reaction flask, and stirred for 2 minutes. 2-Naphthalenethiol (0.0801 g, 0.5 mmol) and chlorobenzene (1 mL) were added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 50%.

Example 15: $[La(CH_3CN)_9]^{3+}[(AlCl_4)_3]^{3-} \cdot CH_3CN$ Catalyzed Reaction of 2-Hydroxychalcone to Prepare Cyclopenta[c]Chromene Compound $[La(CH_3CN)_9]^{3+}[(AlCl_4)_3]^{3-} \cdot CH_3CN$ (0.0158 g, 0.015 mmol, 3 mol %), 2-hydroxychalcone (0.1121 g, 0.5 mmol) and chlorobenzene (1 mL) were added into a dehydrated and deoxidized reaction flask, and stirred for 2 minutes. 2-Naphthalenethiol (0.0961 g, 0.6 mmol) and chlorobenzene (1 mL) were added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 66%.

Example 16: $[Nd(CH_3CN)_9]^{3+}[(AlCl_4)_3]^{3-} \cdot CH_3CN$ Catalyzed Reaction of 2-Hydroxychalcone to Prepare Cyclopenta[c]Chromene Compound $[Nd(CH_3CN)_9]^{3+}[(AlCl_4)_3]^{3-} \cdot CH_3CN$ (0.0159 g, 0.015 mmol, 3 mol %), 2-hydroxychalcone (0.1121 g, 0.5 mmol) and chlorobenzene (1 mL) were added into a dehydrated and deoxidized reaction flask, and stirred for 2 minutes. 2-Naphthalenethiol (0.0961 g, 0.6 mmol) and chlorobenzene (1 mL) were added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 58%.

Example 17: $[Sm(CH_3CN)_9]^{3+}[(AlCl_4)_3]^{3-} \cdot CH_3CN$ Catalyzed Reaction of 2-Hydroxychalcone to Prepare Cyclopenta[c]Chromene Compound $[Sm(CH_3CN)_9]^{3+}[(AlCl_4)_3]^{3-} \cdot CH_3CN$ (0.0159 g, 0.015 mmol, 3 mol %), 2-hydroxychalcone (0.1121 g, 0.5 mmol) and chlorobenzene (1 mL) were added into a dehydrated and deoxidized reaction flask, and stirred for 2 minutes. 2-Naphthalenethiol (0.0961 g, 0.6 mmol) and chlorobenzene (1 mL) were added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 61%.

Example 18: $[Gd(CH_3CN)_9]^{3+}[(AlCl_4)_3]^{3-} \cdot CH_3CN$ Catalyzed Reaction of 2-Hydroxychalcone to Prepare Cyclopenta[c]Chromene Compound $[Gd(CH_3CN)_9]^{3+}[(AlCl_4)_3]^{3-} \cdot CH_3CN$ (0.0161 g, 0.015 mmol, 3 mol %), 2-hydroxychalcone (0.1121 g, 0.5 mmol) and chlorobenzene (1 mL) were added into a dehydrated and deoxidized reaction flask, and stirred for 2 minutes. 2-Naphthalenethiol (0.0961 g, 0.6 mmol) and chlorobenzene (1 mL) were added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 64%.

Example 19: $[Yb(CH_3CN)_9]^{3+}[(AlCl_4)_3]^{3-} \cdot CH_3CN$ Catalyzed Reaction of 3-(3-chloro-2-hydroxyphenyl)-1-phenyl-2-propene-1-one to Prepare Cyclo-Penta[c]Chromene Compound $[Yb(CH_3CN)_9]^{3+}[(AlCl_4)_3]^{3-} \cdot CH_3CN$ (0.0273 g, 0.025 mmol, 5 mol %), 3-(3-chloro-2-hydroxyphenyl)-1-phenyl-2-propene-1-one (0.1293 g, 0.5 mmol) and chlorobenzene (1 mL) were added into a dehydrated and deoxidized reaction flask, stirred for 2 minutes. 2-Naphthalenethiol (0.0961 g, 0.6 mmol) and chlorobenzene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 62%.

The theoretical molecular formula and NMR spectrum of the product obtained are shown below. It can be seen from the analysis that the actual synthesized product is consistent with the theoretical analysis.

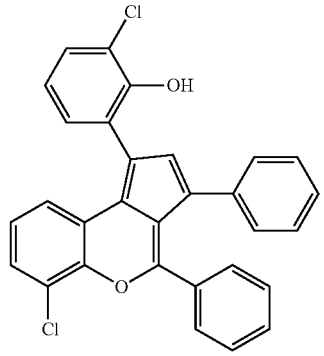 [SMILES: Oc1c(Cl)cccc1-c1cc(-c2ccccc2)c2c(-c3ccccc3)oc3c(Cl)cccc3c1-2]

$^1$H NMR (400 MHz, CDCl$_3$) δ 7.57 (dd, J=8.0, 1.2 Hz, 1H), 7.54-7.52 (m, 2H), 7.42-7.36 (m, 3H), 7.33-7.29 (m, 1H), 7.17-7.10 (m, 4H), 7.03-7.01 (m, 5H), 6.99-6.97 (m, 1H), 5.77 (s, 1H).

Example 20: $[Yb(CH_3CN)_9]^{3+}[(AlCl_4)_3]^{3-} \cdot CH_3CN$ Catalyzed Reaction of 3-(3-chloro-2-hydroxyphenyl)-1-phenyl-2-propene-1-one to Prepare Cyclo-Penta[c]Chromene Compound $[Yb(CH_3CN)_9]^{3+}[(AlCl_4)_3]^{3-} \cdot CH_3CN$ (0.0273 g, 0.025 mmol, 3 mol %), 3-(4-chloro-2-hydroxyphenyl)-1-phenyl-2-propen-1-one (0.1293 g, 0.5 mmol) and acetonitrile (1 mL) were added into a dehydrated and deoxidized reaction flask, stirred for 2 minutes. 2-Naphthalenethiol (0.0961 g, 0.6 mmol) and acetonitrile (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 73%.

The theoretical molecular formula and NMR spectrum of the product obtained are shown below. It can be seen from the analysis that the actual synthesized product is consistent with the theoretical analysis.

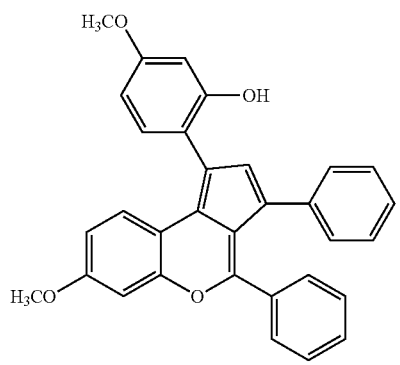

$^1$H NMR (400 MHz, CDCl$_3$) δ 7.63 (d, J=9.2 Hz, 1H), 7.46-7.44 (m, 2H), 7.35-7.28 (m, 2H), 7.17-7.13 (m, 2H), 7.09 (d, J=2.8 Hz, 1H), 7.01-6.97 (m, 6H), 6.88 (dd, J=8.8, 2.8 Hz, 1H), 6.68 (d, J=2.4 Hz, 1H), 6.64 (dd, J=8.4, 2.8 Hz, 1H), 5.45 (s, 1H), 3.88 (s, 3H), 3.86 (s, 3H).

Example 22: [Yb(CH$_3$CN)$_9$]$^{3+}$[(AlCl$_4$)$_3$]$^{3-}$·CH$_3$CN Catalyzed Reaction of 3-(5-chloro-2-hydroxyphenyl)-1-phenyl-2-propene-1-ketone to Prepare Cyclo-Penta[c]Chromene Compound

[Yb(CH$_3$CN)$_9$]$^{3+}$[(AlCl$_4$)$_3$]$^{3-}$·CH$_3$CN (0.0163 g, 0.015 mmol, 3 mol %), 3-(5-chloro-2-hydroxyphenyl)-1-phenyl-2-propene-1-ketone (0.1293 g, 0.5 mmol) and chlorobenzene (1 mL) were added into a dehydrated and deoxidized reaction flask, stirred for 2 minutes. 2-Naphthalenethiol (0.0961 g, 0.6 mmol) and chlorobenzene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 68%.

The theoretical molecular formula and NMR spectrum of the product obtained are shown below. It can be seen from the analysis that the actual synthesized product is consistent with the theoretical analysis.

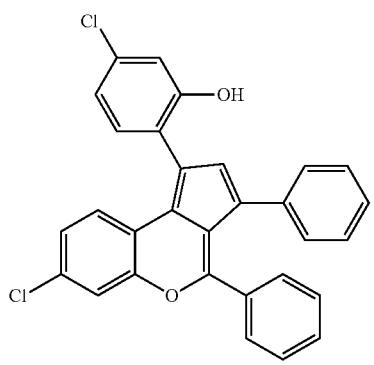 [SMILES: Oc1cc(Cl)ccc1-c1cc(-c2ccccc2)c2c(-c3ccccc3)oc3cc(Cl)ccc3c1-2]

$^1$H NMR (400 MHz, CDCl$_3$) δ 7.62 (d, J=2.0 Hz, 1H), 7.57 (d, J=8.8 Hz, 1H), 7.44-7.42 (m, 2H), 7.35-7.30 (m, 2H), 7.21 (dd, J=8.8, 2.0 Hz, 1H), 7.17-7.13 (m, 2H), 7.11 (d, J=2.0 Hz, 1H), 7.05-6.96 (m, 7H), 5.44 (s, 1H).

Example 21: [Yb(CH$_3$CN)$_9$]$^{3+}$[(AlCl$_4$)$_3$]$^{3-}$·CH$_3$CN Catalyzed Reaction of 3-(2-hydroxy-4-methoxyphenyl)-1-phenyl-2-propene-1-one to Prepare Cyclo-Penta[c]Chromene Compound

[Yb(CH$_3$CN)$_9$]$^{3+}$[(AlCl$_4$)$_3$]$^{3-}$·CH$_3$CN (0.0381 g, 0.035 mmol, 3 mol %), 3-(2-hydroxy-4-methoxyphenyl)-1-phenyl-2-propene-1-one (0.1272 g, 0.5 mmol) and chlorobenzene (1 mL) were added into a dehydrated and deoxidized reaction flask, stirred for 2 minutes. 2-Naphthalenethiol (0.0961 g, 0.6 mmol) and toluene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 69%.

The theoretical molecular formula and min NMR spectrum of the product obtained are shown below. It can be seen from the analysis that the actual synthesized product is consistent with the theoretical analysis.

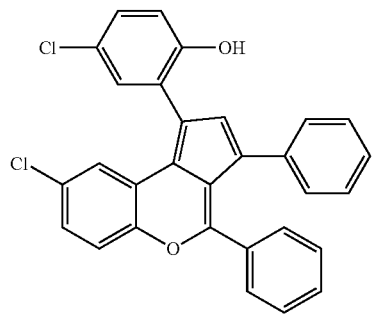

$^1$H NMR (400 MHz, CDCl$_3$) δ 7.61 (d, J=2.4 Hz, 1H), 7.54-7.52 (m, 1H), 7.43-7.41 (m, 3H), 7.32-7.27 (m, 3H), 7.16-7.12 (m, 2H), 7.04-6.95 (m, 7H), 5.39 (s, 1H).

Example 23: [Yb(CH₃CN)₉]³⁺[(AlCl₄)₃]³⁻·CH₃CN Catalyzed Reaction of 3-(5-bromo-2-hydroxyphenyl)-1-phenyl-2-propene-1-ketone to Prepare Cyclo-Penta[c]Chromene Compound

[Yb(CH$_3$CN)$_9$]$^{3+}$[(AlCl$_4$)$_3$]$^{3-}$·CH$_3$CN (0.0163 g, 0.015 mmol, 3 mol %), 3-(5-bromo-2-hydroxyphenyl)-1-phenyl-2-propene-1-ketone (0.1515 g, 0.5 mmol) and chlorobenzene (1 mL) were added into a dehydrated and deoxidized reaction flask, stirred for 2 minutes. 2-Naphthalenethiol (0.0961 g, 0.6 mmol) and chlorobenzene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 68%.

The theoretical molecular formula and NMR spectrum of the product obtained are shown below. It can be seen from the analysis that the actual synthesized product is consistent with the theoretical analysis.

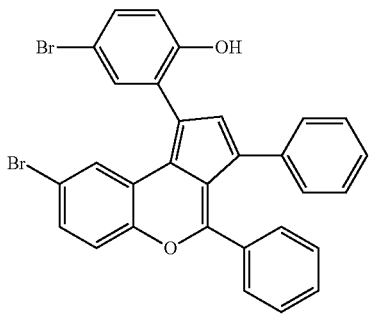 [SMILES: Oc1ccc(Cl)cc1-c1cc(-c2ccccc2)c2c(-c3ccccc3)oc3ccc(Cl)cc3c1-2]

$^1$H NMR (400 MHz, CDCl$_3$) δ 7.78 (d, J=2.0 Hz, 1H), 7.57-7.56 (m, 1H), 7.50-7.43 (m, 5H), 7.34-7.31 (m, 1H), 7.17-7.13 (m, 2H), 7.05-6.96 (m, 7H), 5.37 (s, 1H).

Example 24: [Yb(CH₃CN)₉]³⁺[(AlCl₄)₃]³⁻·CH₃CN Catalyzed Reaction of 3-(2-hydroxy-5-methylphenyl)-1-phenyl-2-propene-1-ketone to Prepare Cyclo-Penta[c]Chromene Compound

[Yb(CH$_3$CN)$_9$]$^{3+}$[(AlCl$_4$)$_3$]$^{3-}$·CH$_3$CN (0.0163 g, 0.015 mmol, 3 mol %), 3-(2-hydroxy-5-methylphenyl)-1-phenyl-2-propene-1-ketone (0.1191 g, 0.5 mmol) and chlorobenzene (1 mL) were added into a dehydrated and deoxidized reaction flask, stirred for 2 minutes. 2-Naphthalenethiol (0.0961 g, 0.6 mmol) and chlorobenzene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 82%.

The theoretical molecular formula and NMR spectrum of the product obtained are shown below. It can be seen from the analysis that the actual synthesized product is consistent with the theoretical analysis.

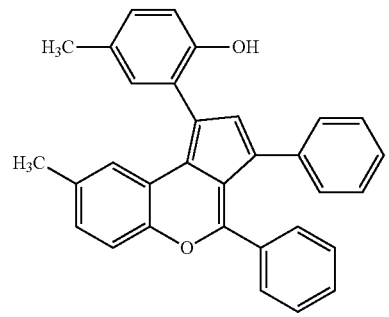 [SMILES: Cc1ccc(O)c(-c2cc(-c3ccccc3)c3c(-c4ccccc4)oc4ccc(C)cc4c2-3)c1]

$^1$H NMR (400 MHz, CDCl$_3$) δ 7.52-7.47 (m, 2H), 7.46-7.44 (m, 2H), 7.30-7.26 (m, 2H), 7.15-7.11 (m, 4H), 7.06 (s, 1H), 7.00-6.98 (m, 6H), 5.27 (s, 1H), 2.35 (s, 3H), 2.28 (s, 3H).

Example 25: [Yb(CH₃CN)₉]³⁺[(AlCl₄)₃]³⁻·CH₃CN Catalyzed Reaction of 3-(2-hydroxy-5-methoxyphenyl)-1-phenyl-2-propene-1-one to Prepare Cyclo-Penta[c]Chromene Compound

[Yb(CH$_3$CN)$_9$]$^{3+}$[(AlCl$_4$)$_3$]$^{3-}$·CH$_3$CN (0.0163 g, 0.015 mmol, 3 mol %), 3-(2-hydroxy-5-methoxyphenyl)-1-phenyl-2-propene-1-one (0.1271 g, 0.5 mmol) and chlorobenzene (1 mL) were added into a dehydrated and deoxidized reaction flask, stirred for 2 minutes. 2-Naphthalenethiol (0.0961 g, 0.6 mmol) and chlorobenzene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 77%.

The theoretical molecular formula and NMR spectrum of the product obtained are shown below. It can be seen from the analysis that the actual synthesized product is consistent with the theoretical analysis.

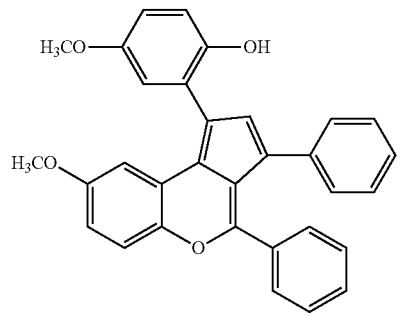 [SMILES: COc1ccc(O)c(-c2cc(-c3ccccc3)c3c(-c4ccccc4)oc4ccc(OC)cc4c2-3)c1]

$^1$H NMR (400 MHz, CDCl$_3$) δ 7.44 (d, J=9.2 Hz, 1H), 7.38-7.36 (m, 2H), 7.23-7.20 (m, 1H), 7.09-7.04 (m, 3H), 7.01 (s, 1H), 6.95-6.92 (m, 7H), 6.87-6.80 (m, 2H), 5.07 (s, 1H), 3.71 (s, 3H), 3.50 (s, 3H).

Example 26: [Yb(CH₃CN)₉]³⁺[(AlCl₄)₃]³⁻·CH₃CN Catalyzed Reaction of 3-(2-chloro-6-hydroxyphenyl)-1-phenyl-2-propene-1-one to Prepare Cyclo-Penta[c]Chromene Compound

[Yb(CH₃CN)₉]³⁺[(AlCl₄)₃]³⁻·CH₃CN (0.0273 g, 0.025 mmol, 5 mol %), 3-(2-chloro-6-hydroxyphenyl)-1-phenyl-2-propene-1-one (0.1293 g, 0.5 mmol) and chlorobenzene (1 mL) were added into a dehydrated and deoxidized reaction flask, stirred for 2 minutes. 2-Naphthalenethiol (0.0961 g, 0.6 mmol) and chlorobenzene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 65%.

The theoretical molecular formula and NMR spectrum of the product obtained are shown below. It can be seen from the analysis that the actual synthesized product is consistent with the theoretical analysis.

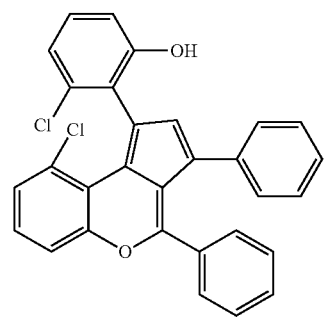 [SMILES: Oc1cccc(Cl)c1-c1cc(-c2ccccc2)c2c(-c3ccccc3)oc3cccc(Cl)c3c1-2]

$^1$H NMR (400 MHz, CDCl₃) δ 7.53 (dd, J=8.0, 1.2 Hz, 1H), 7.43-7.41 (m, 2H), 7.36 (dd, J=7.6, 1.2 Hz, 1H), 7.30-7.24 (m, 3H), 7.16-7.11 (m, 4H), 7.06 (dd, J=8.0, 1.2 Hz, 1H), 7.01-7.00 (m, 4H), 6.89 (dd, J=8.0, 0.8 Hz, 1H), 5.33 (s, 1H).

Example 27: [Yb(CH₃CN)₉]³⁺[(AlCl₄)₃]³⁻·CH₃CN Catalyzed Reaction of 1-(3-chlorophenyl)-3-(2-hydroxyphenyl)-2-propene-1-one to Prepare Cyclo-Penta[c]Chromene Compound

[Yb(CH₃CN)₉]³⁺[(AlCl₄)₃]³⁻·CH₃CN (0.0273 g, 0.025 mmol, 5 mol %), 1-(3-chlorophenyl)-3-(2-hydroxyphenyl)-2-propene-1-one (0.1293 g, 0.5 mmol) and chlorobenzene (1 mL) were added into a dehydrated and deoxidized reaction flask, stirred for 2 minutes. 2-Naphthalenethiol (0.0961 g, 0.6 mmol) and chlorobenzene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 55%.

The theoretical molecular formula and NMR spectrum of the product obtained are shown below. It can be seen from the analysis that the actual synthesized product is consistent with the theoretical analysis.

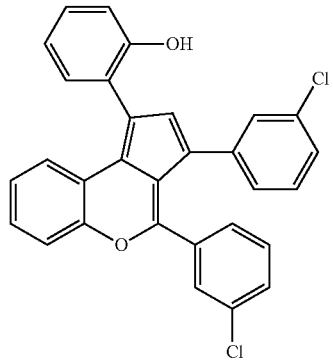 [SMILES: Oc1ccccc1-c1cc(-c2cccc(Cl)c2)c2c(-c3cccc(Cl)c3)oc3ccccc3c1-2]

$^1$H NMR (400 MHz, CDCl₃) δ 7.70 (dd, J=8.4, 1.2 Hz, 1H), 7.61 (d, J=8.0 Hz, 1H), 7.46-7.45 (m, 1H), 7.43 (dd, J=7.6, 1.2 Hz, 1H), 7.40-7.33 (m, 4H), 7.24-7.23 (m, 1H), 7.16 (t, J=8.0 Hz, 1H), 7.11-7.08 (m, 2H), 7.06-7.04 (m, 2H), 7.00 (t, J=7.6 Hz, 1H), 6.95-6.92 (m, 2H), 5.33 (s, 1H).

Example 28: [Yb(CH₃CN)₉]³⁺[(AlCl₄)₃]³⁻·CH₃CN Catalyzed the Reaction of 1-(3-bromophenyl)-3-(2-hydroxyphenyl)-2-propen-1-one to Prepare Cyclopenta[c]Chromene Compound

[Yb(CH₃CN)₉]³⁺[(AlCl₄)₃]³⁻·CH₃CN (0.0381 g, 0.035 mmol, 7 mol %), 1-(3-bromophenyl)-3-(2-hydroxyphenyl)-2-propen-1-one (0.1515 g, 0.5 mmol) and chlorobenzene (1 mL) were added into a dehydrated and deoxidized reaction flask, stirred for 2 minutes. 2-Naphthalenethiol (0.0961 g, 0.6 mmol) and chlorobenzene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 54%.

The theoretical molecular formula and NMR spectrum of the product obtained are shown as below. It can be seen from the analysis that the actual synthesized product is consistent with the theoretical analysis.

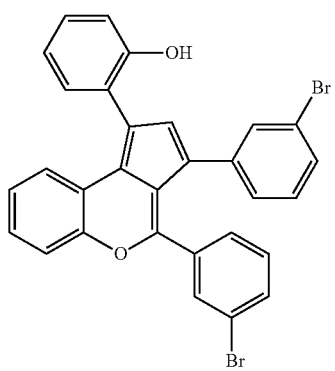 [SMILES: Oc1ccccc1-c1cc(-c2cccc(Br)c2)c2c(-c3cccc(Br)c3)oc3ccccc3c1-2]

$^1$H NMR (400 MHz, CDCl$_3$) δ 7.69 (d, J=8.0 Hz, 1H), 7.61-7.59 (m, 2H), 7.50 (d, J=8.0 Hz, 1H), 7.43-7.41 (m, 2H), 7.38-7.34 (m, 2H), 7.26-7.24 (m, 1H), 7.21-7.19 (m, 1H), 7.13-7.06 (m, 5H), 7.01-6.93 (m, 2H), 5.35 (s, 1H).

Example 29: [Yb(CH$_3$CN)$_9$]$^{3+}$[(AlCl$_4$)$_3$]$^{3-}$·CH$_3$CN Catalyzed Reaction of 3-(2-hydroxyphenyl)-1-(3-methoxyphenyl)-2-propen-1-one to Prepare Cyclopenta[c]Chromene Compound

[Yb(CH$_3$CN)$_9$]$^{3+}$[(AlCl$_4$)$_3$]$^{3-}$·CH$_3$CN (0.0163 g, 0.015 mmol, 3 mol %), 3-(2-hydroxyphenyl)-1-(3-methoxyphenyl)-2-propen-1-one (0.1271 g, 0.5 mmol) and chloro-benzene (1 mL) were added into a dehydrated and deoxidized reaction flask, stirred for 2 minutes. 2-Naphthalenethiol (0.0961 g, 0.6 mmol) and chlorobenzene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 75%.

The theoretical molecular formula and NMR spectrum of the product obtained are shown below. It can be seen from the analysis that the actual synthesized product is consistent with the theoretical analysis.

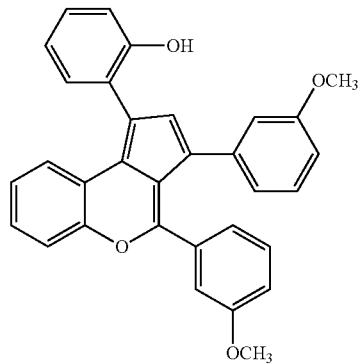 [SMILES: COc1cccc(-c2cc(-c3ccccc3O)c3c4ccccc4oc(-c4cccc(OC)c4)c2-3)c1]

$^1$H NMR (400 MHz, CDCl$_3$) δ 7.70 (dd, J=8.0, 1.2 Hz, 1H), 7.58 (d, J=8.4 Hz, 1H), 7.44 (dd, J=7.6, 1.2 Hz, 1H), 7.36-7.30 (m, 2H), 7.22-7.18 (m, 2H), 7.11-6.97 (m, 5H), 6.89-6.87 (m, 2H), 6.74 (d, J=7.6 Hz, 1H), 6.61 (dd, J=8.0, 2.0 Hz, 1H), 6.47-6.46 (m, 1H), 5.49 (s, 1H), 3.48 (s, 3H), 3.47 (s, 3H).

Example 30: [Yb(CH$_3$CN)$_9$]$^{3+}$[(AlCl$_4$)$_3$]$^{3-}$·CH$_3$CN Catalyzed Reaction of 1-(4-chlorophenyl)-3-(2-hydroxyphenyl)-2-propene-1-ketone to Prepare Cyclopenta[c]Chromene Compound

[Yb(CH$_3$CN)$_9$]$^{3+}$[(AlCl$_4$)$_3$]$^{3-}$·CH$_3$CN (0.0163 g, 0.015 mmol, 3 mol %), 1-(4-chlorophenyl)-3-(2-hydroxyphenyl)-2-propene-1-ketone (0.1293 g, 0.5 mmol) and chloro-benzene (1 mL) were added into a dehydrated and deoxidized reaction flask, stirred for 2 minutes. 2-Naphthalenethiol (0.0961 g, 0.6 mmol) and chlorobenzene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 70%.

The theoretical molecular formula and NMR spectrum of the product obtained are shown below. It can be seen from the analysis that the actual synthesized product is consistent with the theoretical analysis.

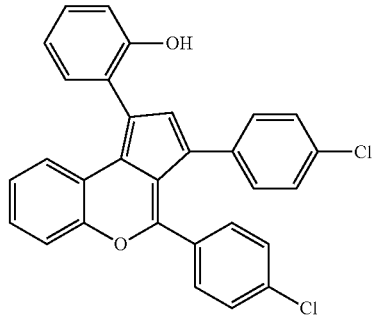 [SMILES: Oc1ccccc1-c1cc(-c2ccc(Cl)cc2)c2c(-c3ccc(Cl)cc3)oc3ccccc3c1-2]

$^1$H NMR (400 MHz, CDCl$_3$) δ 7.69 (dd, J=8.4, 1.6 Hz, 1H), 7.59 (dd, J=8.4, 1.2 Hz, 1H), 7.45-7.33 (m, 5H), 7.25 (t, J=3.6 Hz, 1H), 7.23-7.16 (m, 2H), 7.12-6.99 (m, 5H), 6.92 (d, J=8.4 Hz, 2H), 5.33 (s, 1H).

Example 31: [Yb(CH$_3$CN)$_9$]$^{3+}$[(AlCl$_4$)$_3$]$^{3-}$·CH$_3$CN Catalyzed Reaction of 1-(4-bromo-phenyl)-3-(2-hydroxyphenyl)-2-propene-1-ketone to Prepare Cyclopenta[c]Chromene Compound

[Yb(CH$_3$CN)$_9$]$^{3+}$[(AlCl$_4$)$_3$]$^{3-}$·CH$_3$CN (0.0163 g, 0.015 mmol, 3 mol %), 1-(4-bromophenyl)-3-(2-hydroxyphenyl)-2-propene-1-ketone (0.1515 g, 0.5 mmol) and chloro-benzene (1 mL) were added into a dehydrated and deoxidized reaction flask, stirred for 2 minutes. 2-Naphthalenethiol (0.0961 g, 0.6 mmol) and chlorobenzene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 80%.

The theoretical molecular formula and main NMR test data of the products obtained are as follows. It can be seen from the analysis that the actual synthesized product is consistent with the theoretical analysis.

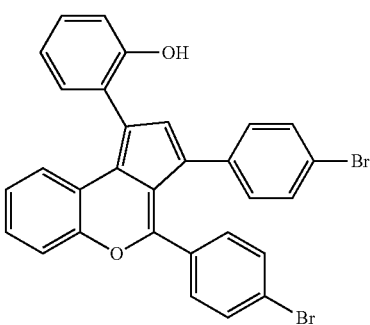 [SMILES: Oc1ccccc1-c1cc(-c2ccc(Br)cc2)c2c(-c3ccc(Br)cc3)oc3ccccc3c1-2]

¹H NMR (400 MHz, CDCl₃) δ 7.68 (dd, J=8.0, 1.6 Hz, 1H), 7.57 (dd, J=8.4, 1.2 Hz, 1H), 7.41 (dd, J=7.6, 1.6 Hz, 1H), 7.37-7.28 (m, 6H), 7.24-7.20 (m, 1H), 7.16 (d, J=8.4 Hz, 2H), 7.09-7.03 (m, 3H), 6.82 (d, J=8.4 Hz, 2H), 5.34 (s, 1H).

Example 32: [Yb(CH₃CN)₉]³⁺[(AlCl₄)₃]³⁻·CH₃CN Catalyzes the Reaction of 1-(4-[1,1'-biphenyl])-3-(2-hydroxybenzene)-2-propen-1-one to Prepare Cyclopenta[c]Chromene Compound

[Yb(CH₃CN)₉]³⁺[(AlCl₄)₃]³⁻·CH₃CN (0.0163 g, 0.015 mmol, 3 mol %), 1-(4-[1,1'-biphenyl])-3-(2-hydroxybenzene)-2-propen-1-one (0.1501 g, 0.5 mmol) and chlorobenzene (1 mL) were added into a dehydrated and deoxidized reaction flask, stirred for 2 minutes. 2-Naphthalenethiol (0.0961 g, 0.6 mmol) and chlorobenzene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 70%.

The theoretical molecular formula and NMR spectrum of the product obtained are shown below. It can be seen from the analysis that the actual synthesized product is consistent with the theoretical analysis.

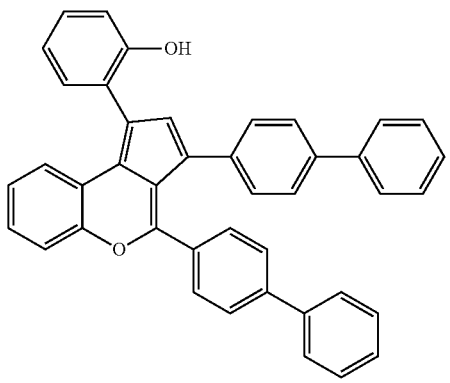 [SMILES: Oc1ccccc1-c1cc(-c2ccc(-c3ccccc3)cc2)c2c(-c3ccc(-c4ccccc4)cc3)oc3ccccc3c1-2]

¹H NMR (400 MHz, CDCl₃) δ 7.72 (dd, J=8.0, 1.6 Hz, 1H), 7.61 (dd, J=8.0, 1.2 Hz, 1H), 7.52-7.49 (m, 2H), 7.46 (dd, J=7.2, 1.6 Hz, 1H), 7.42-7.39 (m, 4H), 7.35-7.27 (m, 10H), 7.24-7.18 (m, 3H), 7.12-7.10 (m, 2H), 7.07-7.03 (m, 3H), 5.45 (s, 1H).

Example 33: [Yb(CH₃CN)₉]³⁺[(AlCl₄)₃]³⁻·CH₃CN Catalyzed Reaction of 3-(2-hydroxyphenyl)-1-(4-methoxyphenyl)-2-propen-1-one to Prepare Cyclopenta[c]Chromene Compound

[Yb(CH₃CN)₉]³⁺[(AlCl₄)₃]³⁻·CH₃CN (0.0163 g, 0.015 mmol, 3 mol %), 3-(2-hydroxyphenyl)-1-(4-methoxyphenyl)-2-propen-1-one (0.1271 g, 0.5 mmol) and chlorobenzene (1 mL) were added into a dehydrated and deoxidized reaction flask, stirred for 2 minutes. 2-Naphthalenethiol (0.0961 g, 0.6 mmol) and chlorobenzene (1 mL) were then added, stirred and refluxed for 36 hours after mixing. Water was added to quench the reaction, extracting three times with ethyl acetate (10 mL×3), drying the extract with anhydrous sodium sulfate, filtering, removing the solvent under reduced pressure, and finally running flash column chromatography on a silica gel column (Eluent: V ethyl acetate:V petroleum ether is 1:20 to 1:15) to obtain a red-brown solid. The solid was placed under an oil pump and continued to be dried for about one day. The yield was 74%.

The theoretical molecular formula and NMR spectrum of the product obtained are shown below. It can be seen from the analysis that the actual synthesized product is consistent with the theoretical analysis.

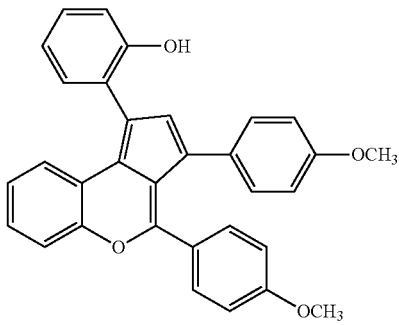 [SMILES: COc1ccc(-c2cc(-c3ccccc3O)c3c4ccccc4oc(-c4ccc(OC)cc4)c2-3)cc1]

¹H NMR (400 MHz, CDCl₃) δ 7.67 (dd, J=8.0, 1.6 Hz, 1H), 7.58-7.56 (m, 1H), 7.45-7.40 (m, 3H), 7.36-7.29 (m, 2H), 7.23-7.17 (m, 1H), 7.10-7.08 (m, 1H), 7.06-7.03 (m, 1H), 7.00 (s, 1H), 6.94 (d, J=8.4 Hz, 2H), 6.67 (d, J=8.8 Hz, 2H), 6.59 (d, J=8.8 Hz, 2H), 5.48 (s, 1H), 3.76 (s, 3H), 3.72 (s, 3H).

The invention claimed is:

1. A method for preparing a cyclopenta[c]chromene compound, comprising the following steps: under anhydrous and anaerobic conditions, a chalcone compound as a reactant, a cationic rare earth metal compound as a catalyst, and 2-naphthalenethiol as an accelerator, react in an organic solvent to prepare the cyclopenta[c]chromene compound;

wherein the cationic rare earth metal compound has the following structure:

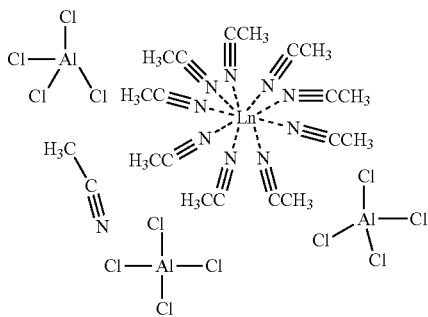

wherein, Ln represents a trivalent rare earth metal ion; wherein the chalcone compound has the following chemical structure:

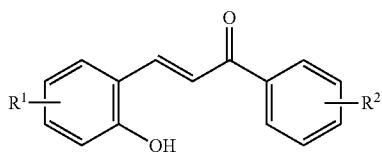

wherein, $R^1$ is selected from the group consisting of hydrogen, 3-chloro, 4-chloro, 4-methoxy, 5-chloro, 5-bromo, 5-methyl, 5-methoxy, and 6-chloro; $R^2$ is selected from the group consisting of hydrogen, 3'-chloro, 3'-bromo, 3'-methoxy, 4'-chloro, 4'-bromo, 4'-phenyl, and 4'-methoxy.

2. The method for preparing the cyclopenta[c]chromene compound according to claim 1, wherein the organic solvent is selected from the group consisting of chlorobenzene, acetonitrile, dichloroethane, and toluene; Ln is selected from the group consisting of La, Nd, Sm, Gd, and Yb; and the anhydrous and anaerobic conditions are an inert atmosphere condition.

3. The method for preparing the cyclopenta[c]chromene compound according to claim 2, wherein the organic solvent is chlorobenzene and Ln is ytterbium.

4. The method for preparing cyclopenta[c]chromene compound according to claim 1, wherein a molar ratio of the catalyst:the chalcone compound:the accelerator is (0.01 to 0.08):1:(0.6 to 1.3).

5. The method for preparing cyclopenta[c]chromene compound according to claim 4, wherein the molar ratio of the catalyst:the chalcone compound:the accelerator is (0.03 to 0.07):1:(1.1 to 1.2).

6. The method for preparing cyclopenta[c]chromene compound according to claim 1, wherein a reaction temperature is 80 to 140° C.; and a reaction time is 24 to 72 hours.

7. The method for preparing cyclopenta[c]chromene compound according to claim 6, wherein the reaction temperature is a reflux temperature of the organic solvent, and the reaction time is 36 hours.

* * * * *